US007009010B2

(12) United States Patent
Kanto et al.

(10) Patent No.: US 7,009,010 B2
(45) Date of Patent: Mar. 7, 2006

(54) WATER-ABSORBENT RESIN AND PRODUCTION PROCESS THEREFOR

(75) Inventors: Teruyuki Kanto, Himeji (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/472,038

(22) PCT Filed: Dec. 17, 2002

(86) PCT No.: PCT/JP02/13160

§ 371 (c)(1),
(2), (4) Date: Sep. 16, 2003

(87) PCT Pub. No.: WO03/051939

PCT Pub. Date: Jun. 26, 2003

(65) Prior Publication Data

US 2004/0110913 A1    Jun. 10, 2004

(30) Foreign Application Priority Data

Dec. 19, 2001    (JP)    ............................. 2001-385730

(51) Int. Cl.
*C08F 2/00*    (2006.01)
(52) U.S. Cl. ................... 526/77; 526/317.1; 526/318.5; 524/556; 528/502; 562/600
(58) Field of Classification Search ............. 526/317.1, 526/318.5, 77; 524/556; 528/502; 562/600
See application file for complete search history.

(56) References Cited

U.S. PATENT DOCUMENTS

| | | | |
|---|---|---|---|
| 4,093,776 A | 6/1978 | Aoki et al. | |
| 4,367,323 A | 1/1983 | Kitamura et al. | |
| 4,446,261 A | 5/1984 | Yamasaki et al. | |
| 4,625,001 A | 11/1986 | Tsubakimoto et al. | |
| 4,683,274 A | 7/1987 | Nakamura et al. | |
| 4,769,427 A | 9/1988 | Nowakowsky et al. | |
| 4,857,610 A | 8/1989 | Chmelir et al. | |
| 4,873,299 A | 10/1989 | Nowakowsky et al. | |
| 4,985,514 A | 1/1991 | Kimura et al. | |
| 5,124,416 A | 6/1992 | Haruna et al. | |
| 5,149,750 A | 9/1992 | Niessner et al. | |
| 5,164,459 A | 11/1992 | Kimura et al. | |
| 5,244,735 A | 9/1993 | Kimura et al. | |
| 5,250,640 A | 10/1993 | Irie et al. | |
| 5,380,808 A * | 1/1995 | Sumiya et al. ........... 526/317.1 | |
| 5,385,983 A | 1/1995 | Graham | |
| 5,409,771 A | 4/1995 | Dahmen et al. | |
| 5,462,972 A | 10/1995 | Smith et al. | |
| 5,597,873 A | 1/1997 | Chambers et al. | |
| 5,610,220 A | 3/1997 | Klimmek et al. | |
| 5,633,316 A | 5/1997 | Gartner et al. | |
| 5,672,633 A | 9/1997 | Brehm et al. | |
| 5,759,358 A * | 6/1998 | Bauer et al. .................. 203/38 |
| 6,071,976 A | 6/2000 | Dairoku et al. | |
| 6,139,742 A * | 10/2000 | Bhattacharyya et al. . 210/500.3 |
| 6,174,978 B1 | 1/2001 | Hatsuda et al. | |
| 6,228,930 B1 | 5/2001 | Dairoku et al. | |
| 6,241,928 B1 | 6/2001 | Hatsuda et al. | |
| 6,254,990 B1 | 7/2001 | Ishizaki et al. | |
| 6,291,636 B1 | 9/2001 | Miyake et al. | |
| 6,444,744 B1 | 9/2002 | Fujimaru et al. | |
| 2002/0120085 A1 * | 8/2002 | Matsumoto et al. ..... 526/317.1 |

FOREIGN PATENT DOCUMENTS

| | | |
|---|---|---|
| EP | 0 349 240 A2 | 1/1990 |
| EP | 0 450 923 A2 | 10/1991 |
| EP | 0 450 924 A2 | 10/1991 |
| EP | 0 574 260 A1 | 12/1993 |
| EP | 0 605 150 A1 | 7/1994 |
| EP | 0 605 150 B1 | 7/1994 |
| EP | 0 668 080 A2 | 8/1995 |
| EP | 0 812 873 A1 | 12/1997 |
| EP | 0 942 014 A2 | 9/1999 |
| EP | 1 178 059 | 2/2002 |
| EP | 1 260 527 A2 | 11/2002 |
| EP | 1 302 485 A1 | 4/2003 |

(Continued)

*Primary Examiner*—Bernard Lipman
(74) *Attorney, Agent, or Firm*—Roylance, Abrams, Berdo & Goodman, L.L.P.

(57) ABSTRACT

To provide: a process in which a coarse gel itself is made not to form in the case of applying the aqueous solution polymerization; and a process in which the polymerization is mildly controlled and the production is stably carried out in the case of applying the reversed-phase suspension polymerization or static polymerization, in a production of a water-absorbent resin. In a production process for a water-absorbent resin, which comprises a polymerization step that includes the steps of: carrying out polymerization, involving crosslinking, of an aqueous solution of a water-soluble unsaturated monomer including acrylic acid(salt); and at the same time carrying out fine division of the resultant hydrogel, or in a production process for a water-absorbent resin, which comprises the steps of: carrying out polymerization, involving crosslinking, of an aqueous solution of a water-soluble unsaturated monomer including acrylic acid(salt); and carrying out fine division of the resultant hydrogel, or in a production process for a water-absorbent resin, which comprises a polymerization step that includes the steps of: carrying out polymerization, involving crosslinking, of an aqueous solution of a water-soluble unsaturated monomer including acrylic acid(salt); and at the same time obtaining a finely divided hydrogel, the water-soluble unsaturated monomer is adjusted in order to contain furfural in an amount of 11 to 1,000 weight ppm (relative to the monomer).

38 Claims, No Drawings

FOREIGN PATENT DOCUMENTS

| | | |
|---|---|---|
| JP | 3-31306 | 2/1991 |
| JP | 4-255701 | 9/1992 |
| JP | 6-107800 | 4/1994 |
| JP | 6-142612 | 5/1994 |
| JP | 6-211934 | 8/1994 |
| JP | 7-82210 | 3/1995 |
| JP | 7-224204 | 8/1995 |
| JP | 7-242709 | 9/1995 |
| JP | 11-71529 | 3/1999 |
| JP | 11-322846 | 11/1999 |
| JP | 2002-212204 | 7/2002 |
| WO | WO 94/15971 | 7/1994 |
| WO | WO 95/22356 | 8/1995 |
| WO | WO 99/42494 | 8/1999 |
| WO | WO 99/42496 | 8/1999 |
| WO | WO 99/43720 | 9/1999 |
| WO | WO 00/24810 | 5/2000 |
| WO | WO 01/38402 A1 | 5/2001 |

\* cited by examiner

WATER-ABSORBENT RESIN AND PRODUCTION PROCESS THEREFOR

TECHNICAL FIELD

The present invention relates to a production process for a water-absorbent resin. More particularly, the present invention relates to a production process for a water-absorbent resin, comprising a polymerization step that includes the steps of: carrying out polymerization, involving crosslinking, of an aqueous solution of a water-soluble unsaturated monomer including acrylic acid (salt); and at the same time carrying out fine division of the resultant hydrogel, in which the various properties, polymerization rate, and drying rate are enhanced by carrying out the fine division of the gel uniformly.

BACKGROUND ART

In recent years, water-absorbent resins having excellent water absorbency are developed and widely used mainly for disposable uses, as absorbent articles (e.g. disposable diapers and sanitary napkins), and further water-retaining agents in agricultural and horticultural fields and water-holding materials in engineering works fields.

The above water-absorbent resins are made water-swellable and water-insoluble by slightly crosslinking hydrophilic polymers. Generally, as to the production process thereof, they have been obtained as powders by a process including the steps of: carrying out polymerization of water-soluble unsaturated monomers such as acrylic acid; and crosslinking the resultant polymers during or after the polymerization. Accordingly, many polymerization methods for obtaining powdery water-absorbent resins (e.g. reversed-phase suspension polymerization, aqueous solution polymerization, and further precipitation polymerization which involves precipitating a polymer in a solvent, bulk polymerization which involves polymerization substantially in the absence of a solvent, and spray polymerization which involves polymerization in gas phase) have been proposed hitherto. Among these polymerization methods, the aqueous solution polymerization and reversed-phase suspension polymerization are mainly used in view of performance and easiness of controlling the polymerization.

The reversed-phase suspension polymerization is a polymerization method which involves dispersing an aqueous monomer solution in a hydrophobic organic solvent in the form of particles having particle diameters of about 1 to about 0.1 mm, and has the advantage of obtaining gel particles having particle diameters of products at the same time as the polymerization (for example, as is mentioned in such as specifications of U.S. Pat. Nos. 4,093,776, 4,367,323, 4,446,261, and 4,683,274, and especially refer to the following patent document 1.).

However, the control of the polymerization temperature is difficult in the reversed-phase suspension polymerization which is carried out by being dispersed in a large quantity of solvent. Especially, there is danger of explosion during the polymerization when the concentration is raised (for example, the concentration of the aqueous monomer solution is not less than 40 weight %). Therefore, there are problems such that the productivity in an increasing scale cannot be improved sufficiently.

In addition, the aqueous solution polymerization is a method which involves polymerizing an aqueous monomer solution without using a dispersible solvent, and is excellent in costs, productivity, and safety of products because the polymerization can be carried out by using water only. These aqueous solution polymerizations are further roughly divided into a method which involves static polymerization such as belt polymerization (for example, as is mentioned in such as specifications of U.S. Pat. Nos. 6,174,978 and 4,857,610, and especially refer to the following patent document 2.), and a method which involves polymerization while being stirred with such as kneaders (stirring polymerization). In the above aqueous solution polymerization that is different from the reversed-phase suspension polymerization, obtained is a massive gel having a size of far larger than particle diameters of products. Therefore, the fine division of the gel is necessary for drying and production. When polymerization vessels having shearing force (e.g. kneaders) are used as polymerization machines in the above stirring polymerization, the gel is finely divided at the same time as the polymerization. Therefore, a step of finely dividing the gel after the polymerization is unnecessary, and the specific surface area of the gel is large during the polymerization. Accordingly, the stirring polymerization has the advantage of easily removing polymerization heat and also having high productivity.

The above stirring polymerization carried out by using such as kneaders is a production process for a water-absorbent resin, comprising a polymerization step including the steps of: supplying an aqueous solution of a water-soluble unsaturated monomer to a polymerization vessel having shearing force to carry out polymerization involving crosslinking; and at the same time finely dividing the resultant hydrogel (for example, as is exemplified in such as: specifications of U.S. Pat. Nos. 4,625,001, 4,985,514, and 5,124,416 filed by Nippon Shokubai Co., Ltd.; and a pamphlet of WO 01/38402 and specifications of U.S. Pat. Nos. 5,149,750, 4,769,427, and 4,873,299 filed by BASF, and especially refer to the following patent documents 3 and 4.).

However, in the above production process for a water-absorbent resin, comprising a polymerization step including the steps of: carrying out polymerization including crosslinking; and at the same time finely dividing the resultant gel, the gel is finely divided into pieces having particle diameters of about 1 mm during the polymerization, but there are many cases where the fine division of the gel carried out at the same time as the polymerization takes longer time than the polymerization time. Therefore, there are cases where the polymerization time is unnecessarily prolonged for carrying out the fine division sufficiently, or where the lowering of properties is caused because of the longtime fine division (shearing) of the gel.

Furthermore, the hydrogel as discharged from the polymerization vessel in this way is finely divided into a particulate gel having a size of a few millimeter (favorably about 1 to about 3 mm) by shearing force during the polymerization, but the fine division of the gel during the polymerization is usually difficult to completely carry out. There are cases where the resultant finely divided gel is contaminated with such a coarse gel as has a size of larger than a few centimeters in an amount of a few to about 10 weight %.

Particularly, the side-production of the coarse gel tends to increase if an attempt is made to raise the temperature when the polymerization is initiated, or to raise the concentration of the water-soluble unsaturated monomer, or to decrease the extractable content of the water-absorbent resin. Accordingly, in the above production process for a water-absorbent resin, comprising a polymerization step including the steps of: carrying out polymerization involving crosslinking; and at the same time finely dividing the resultant gel, there is a case where: when an attempt is made to decrease the extractable content of the water-absorbent resin, or to raise the temperature when the polymerization is initiated or the concentration of the water-soluble unsaturated monomer in order to improve productivity or properties, the restriction occurs that the coarse gel is side-produced.

In addition, the drying time of the finely divided gel depends upon its specific surface area. Therefore, the contamination with the coarse gel in only a few percents has problems such that: not only the drying rate of the entire finely divided gel is greatly lowered and the longtime drying is necessary, but also the above unnecessarily drying causes the properties to lower, or the properties after the drying are changed or lowered in proportion to the gel particle diameter. In addition, there is a case where the above coarse gel in an amount of few percents is an undried product even after the drying, and there is also a case where the procedure such as pulverization or classification after the drying cannot be carried out (e.g. the pulverization step or classification step after the drying is stopped.) because of the adhesion of the undried product (gel) with which the dried product is contaminated.

Accordingly, as to the coarse gel with which the finely divided gel is contaminated, a method which involves removing the coarse gel by classification after polymerization (for example, as is mentioned in such as a gazette of JP-A-107800/1994, and especially refer to the following patent document 5.) and a method which involves classifying an undried product after drying (for example, as is mentioned in such as a specification of U.S. Pat. No. 6,291,636, and especially refer to the following patent document 6.) are also proposed. However, in the above methods which involve removing the coarse gel or undried product after the polymerization, not only the apparatuses are complicated and the classification efficiency is also low, but also are caused the problems of waste derived from the classified coarse gel and the lowering of yield accompanying the abandonment.

In addition, as to other problems, in the case of carrying out high-temperature polymerization or polymerization in the presence of a transition metal, which includes the reversed-phase suspension polymerization and the static polymerization such as belt polymerization, there have problems such that the stability of monomers is lowered even before the polymerization or during the preparation. In addition, there are also problems of coloring in the water-absorbent resin as obtained.

[Patent Document 1]
Specification of U.S. Pat. No. 5,244,735
[Patent Document 2]
Specification of U.S. Pat. No. 6,241,928
[Patent Document 3]
Specification of U.S. Pat. No. 5,250,640
[Patent Document 4]
Gazette of Japanese Patent No. 2966539
[Patent document 5]
Gazette of JP-A-142612/1994
[Patent Document 6]
Pamphlet of WO 00/24810

DISCLOSURE OF THE INVENTION

Object of the Invention

The present invention has been achieved in consideration of the above present circumstances. That is to say, an object of the present invention is to provide a method, which can solve the above hitherto problems at a stroke in the case where the aqueous solution polymerization (e.g. stirring polymerization and static polymerization) or reversed-phase suspension polymerization is carried out when a water-absorbent resin is produced.

SUMMARY OF THE INVENTION

The present inventor diligently studied to solve the above-mentioned problems. As a result, he have found out that: in the production process for a water-absorbent resin, comprising a polymerization step including the step of: carrying out polymerization, involving crosslinking, of an aqueous solution of a water-soluble unsaturated monomer including acrylic acid (salt); and at the same time carrying out fine division of the resultant hydrogel, and in the production process for a water-absorbent resin, comprising the steps of: carrying out polymerization, involving crosslinking, of an aqueous solution of a water-soluble unsaturated monomer including acrylic acid (salt); and carrying out fine division of the resultant hydrogel, and in the production process for a water-absorbent resin, comprising a polymerization step including the steps of: carrying out polymerization, involving crosslinking, of an aqueous solution of a water-soluble unsaturated monomer including acrylic acid (salt); and at the same time obtaining a finely divided hydrogel, the above problems can be solved at a stroke by making the aforementioned water-soluble unsaturated monomer contain furfural in an amount of 11 to 1,000 weight ppm (relative to the monomer).

That is to say, a production process for a water-absorbent resin, according to the present invention, comprises a polymerization step that includes the steps of: carrying out polymerization, involving crosslinking, of an aqueous solution of a water-soluble unsaturated monomer including acrylic acid (salt); and at the same time carrying out fine division of the resultant hydrogel, with the production process being characterized in that the water-soluble unsaturated monomer contains furfural in an amount of 11 to 1,000 weight ppm (relative to the monomer).

In addition, another production process for a water-absorbent resin, according to the present invention, comprises the steps of: carrying out polymerization, involving crosslinking, of an aqueous solution of a water-soluble unsaturated monomer including acrylic acid (salt); and carrying out fine division of the resultant hydrogel, with the production process being characterized in that:

(A) the water-soluable unsaturated monomer contains furfural in an amount of 11 to 1,000 weight ppm (relative to the monomer);

(B 1) the polymerization is initiated at a temperature of not lower than 30° C. and/or (B2) the water-soluble unsaturated monomer further contains a transition metal; and (C) the resultant finely divided hydrogel has a weight-average particle diameter of 0.3 to 4 mm, and the ratio of coarse gel particles having particle diameters of not smaller than 10 mm is not more than 5 weight % of the finely divided hydrogel.

In addition, yet another production process for a water-absorbent resin, according to the present invention, comprises a polymerization step that includes the steps of: carrying out polymerization, involving crosslinking, of an aqueous solution of a water-soluble unsaturated monomer including acrylic acid (salt); and at the same time obtaining a finely divided hydrogel, with the production process being characterized in that the water-soluble unsaturated monomer contains furfual in an amount of 11 to 1,000 weight ppm (relative to the monomer).

DETAILED DESCRIPTION OF THE INVENTION

Hereinafter, the present invention is further explained in detail.

(1) Water-absorbent Resin:

In the present invention, the water-absorbent resin is said a water-swellable and water-insoluble resin as obtained by introducing a crosslinked structure into a polymer. The term "water-swellable" means ability of absorbing essentially at least 3 times, favorably 5 to 200 times, more favorably 20 to 100 times, as large a quantity of physiological saline as its own weight without load. In addition, the term "water-insoluble" means substantially water-insoluble such that the water-extractable content in the resin is essentially not more than 50 weight (mass) %, favorably not more than 25 weight %, more favorably not more than 15 weight %, still more favorably not more than 10 weight %. Incidentally, these measurement methods are specified in the following examples.

(2) Water-insoluble Unsaturated Monomer:

In addition, the water-absorbent resin includes an acrylic acid (and/or its salt) monomer (and further, favorably in a major proportion) as a water-soluble unsaturated monomer in view of properties in the present invention. The major proportion means that the total molar percentage of the acrylic acid and/or its salt as used is essentially not less than 30 mol %, favorably not less than 50 mol %, more favorably not less than 70 mol %, still more favorably not less than 90 mol %, particularly favorably substantially 100%, relative to the entire monomer as used for the polymerization (except for crosslinking agents). Incidentally, the water-soluble unsaturated monomer means a monomer that is dissolved in water at room temperature in an amount of essentially not smaller than 1 weight %, favorably not smaller than 10 weight %, more favorably not smaller than 30 weight %.

As to the acrylic acid salt usable in the present invention, favorably used in view of properties are acrylic acid monovalent salts (e.g. alkaline metal salts, ammonium salts, and amine salts), and more favorably used are acrylic acid salts of alkaline metals, and still more favorably used are acrylic acid salts as selected from the group consisting of a sodium salt, a lithium salt, and a potassium salt.

As to the water-absorbent resin, the acid group of a polymer is favorably neutralized in a neutralization ratio of 20 to 99 mol %, more favorably 50 to 95 mol %, still more favorably 60 to 90 mol %. As to this neutralization, the monomer before the polymerization may be neutralized, or the polymer during or after the polymerization may be neutralized. Furthermore, both of the neutralization of the monomer and the neutralization of the polymer may be carried out together, but the neutralization of the acrylic acid is favorably carried out. Examples of basic substances usable for the neutralization include (hydrogen) carbonates, hydroxides of alkaline metals, ammonia, and organic amines. The treatment of strong bases (namely, favorably hydroxides of alkaline metals such as sodium hydroxide, potassium hydroxide, and lithium hydroxide, particularly favorably sodium hydroxide) is carried out for improving polymerizability more and obtaining water-absorbent resins having higher properties.

As is shown above, the monomer favorably includes the acrylic acid and/or its salt in a major proportion. However, it may include other monomers together or may include them in a major proportion. Examples of other monomers as included together include water-soluble or hydrophobic unsaturated monomers as copolymerizable components (e.g. methacrylic acid, maleic acid, maleic anhydride, fumaric acid, crotonic acid, itaconic acid, vinylsulfonic acid, 2-(meth)acrylamido-2-methylpropanesulfonic acid, (meth) acryloxylalkanesulfonic acid, and alkaline metal salts and ammonium salts thereof, N-vinyl-2-pyrrolidone, N-vinylacetamide, (meth)acrylamide, N-isopropyl(meth)acrylamide, N,N-dimethyl(meth)acrylamide, 2-hydroxyethyl (meth) acrylate, methoxypolyethylene glycol (meth)acrylate, polyethylene glycol (meth)acrylate, isobutylene, and lauryl (meth)acrylate).

There is no especial limitation on the crosslinking method usable in the present invention, but examples thereof include: (a) a post-crosslinking method which involves obtaining a hydrophilic polymer by carry out polymerization of acrylic acid and/or an acrylic acid salt (if necessary, together with the above water-soluble or hydrophobic unsaturated monomers as copolymerizable components), and thereafter adding a crosslinking agent during or after the polymerization; (b) a radical crosslinking method with radical polymerization initiators; and (c) an radiation-crosslinking method with such as electron beams. However, favorable is (d) a method which involves beforehand adding a predetermined amount of internal-crosslinking agent to acrylic acid and/or an acrylic acid salt, or the above water-soluble or hydrophobic unsaturated monomers as copolymerizable components to carry out polymerization, and subjecting to a crosslinking reaction at the same time as or after the polymerization. Needless to say, both of the crosslinking method (d) and the crosslinking methods (a) to (c) may be carried out together.

As to an internal-crosslinking agent usable in the above method (d), usable is one or at least two internal-crosslinking agents, such as N,N'-methylenebis(meth)acrylamide, (poly)ethylene glycol di(meth)acrylate, (poly)propylene glycol di(meth)acrylate, (polyoxyethylene)trimethylolpropane tri(meth)acrylate, trimethylolpropane di(meth)acrylate, polyethylene glycol di(β-acryloyloxypropionate), trimethylolpropane tri(β-acryloyloxypropionate), poly(meth)allyloxyalkane, (poly)ethylene glycol diglycidyl ether, ethylene glycol, polyethylene glycol, and glycerol. Incidentally, when at least one internal-crosslinking agent is used, it is favorable to essentially use a compound having at least two polymerizable unsaturated groups during the polymerization in consideration of such as absorption properties of the water-absorbent resin as obtained.

The amount of the internal-crosslinking agent as used is favorably in the range of 0.005 to 2 mol %, more favorably 0.01 to 1 mol %, still more favorably 0.05 to 0.2 mol %, relative to the aforementioned monomer component. In the case where the aforementioned amount of the internal-crosslinking agent as used is smaller than 0.005 mol % or larger than 2 mol %, there is a possibility that desirable absorption properties cannot be obtained.

In the case where the water-soluble unsaturated monomer is treated in the state of an aqueous solution in the present invention, the monomer concentration in the above aqueous solution (hereinafter, referred to as an aqueous solution of a water-soluble unsaturated monomer) is not especially limited, but it is favorably in the range of 15 to 70 weight % in view of properties, more favorably in high-concentration conditions where coarse gels are easily caused particularly.

The present invention is preferably applied, for example, in a monomer concentration of still more favorably not less than 20 weight %, particularly favorably not less than 30 weight %, most favorably not less than 40 weight %.

In addition, solvents other than water may be used together, if necessary, and there is no especial limitation on the kinds of the solvents as used together.

Incidentally, when the polymerization is carried out, various properties of the water-absorbent resin may be improved by adding such as various foaming agents, hydrophilic polymers, surfactants, chelating agents, and water-absorbent resin fine powders, or fine powders of the water-absorbent resin may be recycled. There are advantages in that: in a step of the polymerization step, the polymerization involving crosslinking is carried out, and at the same time the resultant hydrogel is finely divided, and therefore the stirring or shearing is carried out during the polymerization, and in that the mixing of these is also carried out easily.

For example, as compounds that are added before or during the polymerization, may be added various foaming agents (e.g. (hydrogen)carbonate salts, carbon dioxide, nitrogen, azo compounds, and inactive organic solvents) in an amount of 0 to 5 weight % (relative to the monomer in terms of solid content), hydrophilic polymers (e.g. starch-cellulose, derivatives of starch-cellulose, polyvinyl alcohol, and water-absorbent resin fine powders or gels thereof) in an amount of 0 to 30 weight % (ditto), various surfactants, and chain transfer agents (e.g. hypophosphorous acid (salts)) in an amount of 0 to 1 weight % (ditto).

(3) Aldehyde Compound (furfural):

In the present invention, it is essential to add an aldehyde compound including furfural to the above water-soluble unsaturated monomer. The amount of this furfural as added is essentially in the range of 11 to 1,000 weight ppm, favorably 25 to 900 weight ppm, more favorably 30 to 600 weight ppm, stil more favorably 50 to 400 weight ppm, particularly favorably 100 to 300 weight ppm, relative to the water-soluble unsaturated monomer. Incidentally, the weight (mass) of the water-soluble unsaturated monomer does not include that of such as a crosslinking agent that is added if necessary.

In the case where the amount of the aldehyde compound (e.g. Furfural) as used is small (namely, the amount of the furfural is smaller than 11 weight ppm, further not larger than 10 weight ppm, more further not larger than 5 weight ppm, still more further not larger than 1 weight ppm), the effect of inhibiting a small amount of coarse gel as side-produced during the polymerization, which is an object of the present invention, is insufficient. Therefore, not only the polymerization time or drying time is unnecessarily prolonged, and further the deterioration of properties is caused, but also, depending on circumstances, there are cases where the pulverization step or classification step after the drying are stopped because of the occurrence and adhesion of undried products after the drying.

In addition, in the cases including the reversed-phase suspension polymerization, it becomes difficult to control the polymerization temperature, and particularly the danger of explosion during the polymerization is increased under a high-concentration condition (for example, the concentration of the aqueous monomer solution is not less than 40 weight %). Particularly, the danger is further increased in the reversed-phase suspension polymerization in which an organic solvent is used in a large quantity. Furthermore, in the case where the high-temperature polymerization or polymerization in the presence of a transition metal is carried out, the stability of the monomer becomes deteriorated in the cases including before the polymerization or during the monomer preparation.

In addition, in the case where the amount of the, aldehyde (e.g. furfural) as used is too much, depending on circumstances, it may cause the properties to lower.

Incidentally, unknown in the present invention is the mechanism which is concerned in that: by the addition of the furfural, the effect of inhibiting the coarse gel is observed, and the polymerization temperature can be mildly controlled, and the stability of the monomer is improved in the case where the high-temperature polymerization or polymerization in the presence of a transition metal is carried out. However, the addition is presumed to favorably control such as shearing, viscoelasticity of the hydrogel as obtained by the polymerization and polymerization rate.

In addition, aldehyde compounds other than the furfural may further be used together in the present invention. Specifically, the aforementioned aqueous solution of the water-soluble unsaturated monomer may further contain aldehyde compounds other than the furfural.

Examples of the aldheyde compounds as used together include compounds selected from aliphatic dialdehydes, aliphatic unsaturated aldehydes, aromatic aldehydes, and heterocyclic aldehydes. As to the molecular weight in view of the effect in the present invention, used together are favorably low-molecular aldehyde compounds, more favorably those having 3 to 20 carbon atoms, still more favorably those having 3 to 10 carbon atoms. Water-soluble aldehyde compounds selected from unsaturated aldehydes, aromatic aldehydes, and heterocyclic aldehydes are favorably used together as the favorable aldehyde compounds. Aldehyde compounds selected from benzaldehyde and acrolein are most favorably used alone and further used together.

The amount of these aldehyde compounds as used together is in the range of 0 to 1,000 weight ppm, favorably 0.1 to 300 weight ppm, more favorably 0.5 to 100 weight ppm, relative to the water-soluble unsaturated monomer. In addition, the weight ratio to the furfual that is an essential component is favorably in the range of 100 to 0, more favorably 80 to 1, more favorably 50 to 2, relative to 100 of the furfural.

In addition, the water-soluble unsaturated monomer favorably further contains a methoxyphenol other than the above aldehyde compounds. Specifically, the aforementioned aqueous solution of the water-soluble unsaturated monomer favorably further contains a methoxyphenol. Specific examples of a methoxyphenol include o-, m-, p-methoxyphenol and methoxyphenol which have at least one substituent such as methyl, t-butyl, or hydroxyl, but particularly p-methoxyphenol is favorably contained. The content of the methoxyphenol is favorably in the range of 0 to 500 weight ppm, more favorably 5 to 200 weight ppm, still more favorably 10 to 160 weight ppm, yet still more favorably 20 to 140 weight ppm, yet still more favorably 30 to 120 weight ppm, yet still more favorably 40 to 100 weight ppm, particularly favorably 50 to 90 weight ppm.

In the present invention, it is essential that the water-soluble unsaturated monomer contains the aldehyde compound including the furfual, but (1) the above furfural may be added to a water-soluble unsaturated monomer in preparation, or (2) the water-soluble unsaturated monomer in the present invention may be prepared by using a monomer containing the furfual in a predetermined amount, or (3) both of the above methods may be carried out together.

Specifically, as to the above (2), the water-soluble unsaturated monomer in the present invention may be prepared by using acrylic acid that contains the furfural in a predetermined amount in the present invention. Specifically, in the present invention, the water-soluble unsaturated monomer in the present invention is also favorably prepared by a process including the steps of synthesizing acrylic acid that purposely contains the furfural, and using the resultant acrylic acid that contains the furfural in a predetermined amount.

That is to say, as to production methods for acrylic acid, such as the propylene gas-phase oxidation method, ethylene cyanohydrin method, high-pressure Reppe method, improved Reppe method, ketene method, and acrylonitrile hydrolysis method have hitherto been known as industrial production methods. Of the above, the gas-phase oxidation method for propylene or propane is most frequently adopted. Then, the intermediate in the production process for acrylic acid contains such as acetic acid, formaldehyde, acrolein, propionic acid, maleic acid, acetone, furfural, and benzaldehyde, as by-products and impurities.

These impurities inhibit the polymerization and make the properties after the polymerization lower. Therefore, subsequently this acrylic acid intermediate (crude acrylic acid) is sufficiently purified. Thereby, these by-products and impurities that inhibit the polymerization are removed as large as possible, and purified acrylic acid containing substantially no furfural (less than 1 ppm) is sold on the market as the acrylic acid. Then, the purified acrylic acid is used as a raw material of water-absorbent resins. In addition, also known are techniques which involve removing impurities such as polymerization inhibitors and dimmers of acrylic acid by purifying acrylic acid when the polymerization of a water-absorbent resin is carried out (such as gazettes of JP-A-211934/1994 and JP-A-031306/1991, and specifications of EP 942014 and EP 574260). Compared with the above prior art, in the present invention, the water-soluble unsaturated monomer in the present invention is also favorably prepared by a process including the steps of synthesizing acrylic acid that purposely contains the furfural, and using the resultant acrylic acid that contains the furfual in a predetermined amount.

In addition, as to the acrylic acid, the content of protoanemonin that is a trace component in the acrylic acid is favorably not more than 20 weight ppm. As the protoanemonin content is increased, not only the polymerization time (time until reaching the polymerization peak temperature) is prolonged, and the residual monomers are increased, but also the water-extractable content is greatly increased in comparison with the slight increase of the water absorption capacity, and thereby the properties are relatively lowered. Accordingly, in view of improving the properties and performance of the water-absorbent resin, the protoanemonin content in the acrylic acid is thought more favorably not more than 10 weight ppm, still more favorably not more than 5 weight ppm, particularly favorably not more than 3 weight ppm, most favorably not more than 1 weight ppm.

(4) Polymerization Step:

In one production process for a water-absorbent resin, according to the present invention, among the above-mentioned many production processes for a water-absorbent resin, applied is a specific polymerization process, namely a production process for a water-absorbent resin, comprising a polymerization step that includes the steps of: supplying the aqueous solution of the water-soluble unsaturated monomer to a polymerization vessel having shear force; and carrying out fine division of the hydrogel as obtained at the same time as the polymerization involving crosslinking. As is mentioned above, the above polymerization process are exemplified in specifications of U.S. Pat. Nos. 4,625,001, 4,985,514, 5,124,416, and 5,250,640, a gazette of Japanese Patent No. 2966539, a pamphlet of WO 01/38402, and specifications of U.S. Pat. Nos. 5,149,750, 4,769,427, and 4,873,299.

Incidentally, in the present invention, the fine division of the hydrogel as obtained at the same time as the polymerization involving crosslinking means a procedure which involves dividing a polymerized hydrogel into at least two pieces while the aqueous solution polymerization goes on, and the fine division is usually carried out by such as rotating rotation paddles in a polymerization vessel having shear force (e.g. a kneader). The fine division in the present invention is not necessarily carried out continually during the polymerization, and may be carried out together with the static polymerization in which the fine division is stopped by such as stopping rotation agitation shafts. The shear force is given to the hydrogel by rotating the rotation agitation shafts, for favorably not less than 30%, more favorably not less than 70%, still more favorably not less than 90%, of the polymerization time.

As to the polymerization vessel having shear force in the present invention, even single-shaft agitation machines can be used, but agitation machines having at least two agitation shafts (e.g. twin-arm kneaders) are favorably used. More favorably used are machines having a rotation agitation shaft in such a manner that the aqueous solution of the water-soluble unsaturated monomer is continuously supplied to the polymerization vessel and the resultant hydrogel is continuously discharged (of the above, machines having at least two rotation agitation shafts). Examples thereof include triple-shaft kneaders (kneader-ruders) having two agitation paddles and one discharging screw, and twin-shaft-extuding kneaders or blenders. The most favorable machines are continuous kneaders having piston flowability, which are machines having two rotation agitation shafts in such a manner that the aqueous solution of the water-soluble unsaturated monomer is continuously supplied to the polymerization vessel and the resultant hydrogel is continuously discharged. Incidentally, the polymerization vessels usable in the present invention are exemplified or shown also in the above patent documents.

Furthermore, the surface roughness of the inner faces of these polymerization vessels is favorably decreased by resin-coating with such as Teflon (registered trade mark) or by electrolysis grinding, and polymerization vessels having stainless-steel-made inner faces are particularly favorably used. Furthermore, the inner faces and agitation shafts of the polymerization vessel are favorably cooled or heated with a jacket. The volume of the polymerization vessel is fitly determined in the range of usually 0.001 to 10 $m^3$, favorably 0.01 to 5 $m^3$, and the aqueous monomer solution is favorably charged in an amount of 10 to 90%, more favorably 20 to 70%, relative to the volume.

In addition, the rotation agitation shafts existing in these polymerization vessels are rotated for at least a predetermined time during the polymerization, and then the fine division of the hydrogel is carried out. The rotation speed may be constant or changeable, or the rotation may be stopped temporarily or intermittently. Specifically, the static polymerization and the rotation polymerization (shear polymerization) may be carried out together in the polymerization vessel having shear force. Furthermore, when at least two agitation shafts are used, these agitation shafts may be rotated in the same direction or in different directions (two directions), but the at least two agitation shafts are favorably in the two directions toward the inside. In addition, the rotation speeds of both may be identical or different.

Specific examples of the polymerization vessels causing shearing action (having shear force) are as follows:

Twin-arm kneader (KEADER, Kurimoto, Ltd.);
Twin-arm kneader-ruder (KNEADER-RUDER, Moriyama Co., Ltd.);
Continuous kneader (CONTINUOUS KNEADER, Dalton Co., Ltd.);
Paddle dryer (PADDLE DRYER, Nara Kikai Seisakasho Co., Ltd.);
KRC kneader (KURIMOTO-READCO CONTINUOUS KNEADER, Kurimoto, Ltd.);
Extruder (EXTRUDER, Kurimoto, Ltd.);
Honda De-Airing Extruder (HONDA DE-AIRING EXTRUDER, Honda Tekko Co., Ltd.)
Chopper (CHOPPER, Hiraga Kosakusho Co., Ltd.);
Twin Dome Gran (TWIN DOME GRAN, Fuji Powdal Co., Ltd.); and
Bivolak (BIVOLAK, Sumitomo Heavy Industries. Ltd.).

Furthermore, in the step of finely dividing the hydrogel as obtained at the same time as the polymerization involving crosslinking, the fine division of the gel is easy during the polymerization, and the coarse gel (for example, having a size of not smaller than 1 cm) is hardly formed because the furfural is used in the present invention. Therefore, it is more favorable for polymerization as initiated at high temperature and polymerization as initiated in high concentration, in which a coarse gel has hitherto been easily formed.

Specifically, the polymerization as carried out is favorably initiated at a temperature of not lower than 20° C., more favorably not lower than 30° C., still more favorably not lower than 40° C., particularly favorably not lower than 50° C. Furthermore, the present invention is favorably applied in a concentration of the aqueous unsaturated monomer of not less than 20 weight %, more favorably not less than 30 weight %, particularly favorably not less than 40 weight %. Even if the above polymerization as initiated at high temperature and polymerization as initiated in high concentration may be carried out in which a coarse gel has hitherto been easily side-produced, or even if a water-absorbent resin having low extractable content is obtained in which a coarse gel is easily side-produced, the present invention has excellent merits such that: the fine division of the gel can be uniformly carried out, and the coarse gel is hardly side-produced. Specifically, the present invention is favorable for a production of a water-absorbent resin having low water-extractable content in which a coarse gel has hitherto been easily side-produced, and the water-extractable content is favorably in the aforementioned range, particularly favorably not less than 15 weight %.

The finely divided hydrogel as obtained in the present invention is discharged from the polymerization vessel and transferred to a subsequent step. The above hydrogel has a uniform particle diameter and very little coarse-gel amount. Usually, the weight-average particle diameter is in the range of 0.3 to 4 mm and the ratio of coarse gel particles having particle diameters of not smaller than 10 mm is not more than 5 weight %.

Specifically, the hydrogel is finely divided until the hydrogel favorably has a weight-average particle diameter of 0.3 to 4 mm, more favorably 0.5 to 3 mm, still more favorably 0.8 to 2 mm. In addition, the coarse gel as decreased relates to a state of having a size of not smaller than 5 cm (favorably not smaller than 1 cm), and the coarse-gel content in the finely divided gel as discharged is also thought favorably not more than 7 weight %, more favorably not more than 5 weight %, still more favorably not more than 3 weight %, particularly favorably not more than 1 weight %, of the entirety. Coarse gels have hitherto been formed in a amount of several percents to several tens percents, but there are advantages in that they can be greatly decreased even in any polymerization condition (e.g. temperature, concentration, and extractable content) in the present invention.

The polymerization pressure (inner pressure of the polymerization vessel) is fitly selected from the group of ordinary pressure, reduced pressure, and compressed pressure, and these may be combined together. Also favorable is a mode such that the polymerization is carried out with distilling out water under reduced pressure in order to lower the boiling temperature. However, the polymerization is more favorably carried out substantially under an ordinary pressure because of such as easiness of operation. In addition, it is favorable to carry out the above polymerization under an ordinary pressure in a gas stream, and to partially remove polymerization heat by evaporation, and the gas stream of such as nitrogen is used.

When the above aqueous monomer solution is polymerized, usable is one or at least two kinds of polymerization initiators, such as potassium persulfate, ammonium persulfate, sodium persulfate, t-butyl hydroperoxide, hydrogen peroxide, 2,2'-azobis(2-amidinopropane) dihydrochloride, 2-hydroxy-1-phenyl-propane-1-one, and benzoin methyl ether. Furthermore, redox initiators are also available by using reductants together to promote decomposition of these polymerization initiators and combining both with each other. Examples of the above reductants include: (bi)sulfurous acid (or its salts) such as sodium sulfite and sodium hydrogensulfite; L-ascorbic acid (or its salts); reducible metals (or their salts) such as ferrous salts; and amines. However, they are not especially limited thereto. The redox polymerization with persulfates and/or hydrogen peroxide is favorably applied. In addition, the amount of these polymerization initiators or reductants as used is in the range of usually 0.001 to 2 mol %, favorably 0.01 to 0.5 mol %.

In addition, in view of promoting the polymerization, the aforementioned aqueous monomer solution that will be polymerized favorably further contains a trace amount of a transition metal, and the polymerization is particularly favorably carried out in the presence of a trace amount of iron. The content of the transition metal as used is favorably in the range of 0 to 5 weight ppm (relative to the monomer in terms of its cation), more favorably 0.1 to 2 weight ppm, particularly favorably 0.2 to 1 weight ppm. In the case where the transition metal is in excess, the residual monomer and the water-extractable content tend to increase. In addition, in the case where the transition metal is little, the polymerization rate tends to decrease.

In addition, instead of using the polymerization initiators, the polymerization reaction may be carried out by irradiating the reaction system with active energy rays, such as radiations, electron beams, and ultraviolet rays, and they may be used together with the polymerization initiators. Incidentally, there is no especial limitation on the reaction temperature and the reaction time in the above polymerization reaction, either, but they may be fitly determined according to such as the kinds of the hydrophilic monomer and the polymerization initiator, and the reaction temperature. The polymerization is usually carried out at a temperature of not higher than a boiling point within 3 hours, favorably within 1 hour, more favorably within 0.5 hour, and is carried out at a peak temperature of not higher than 150° C., still more favorably 90 to 120° C.

(5) Other Polymerization Method:

The present invention, in which the furfural is further used in an amount of 11 to 1,000 weight ppm, can also be applied to other specific polymerization method except the polymerization including carrying out fine division in the polymerization vessel having shear force. Specifically, the present invention can be applied to the high-temperature polymerization or polymerization in the coexistence of a transition metal. Namely, the conditions described in the aforementioned (4) can also be applied to the following specific polymerizations.

That is to say, the present invention also provides a production process for a water-absorbent resin, which comprises the steps of: carrying out polymerization, involving crosslinking, of an aqueous solution of a water-soluble unsaturated monomer including acrylic acid (salt); and carrying out fine division of the resultant hydrogel, with the production process being characterized in that:
(A) the water-soluble unsaturated monomer contains furfural in an amount of 11 to 1,000 weight ppm (relative to the monomer);
(B 1) the polymerization is initiated at a temperature of not lower than 30° C. and/or (B2) the water-soluble unsaturated monomer further contains a transition metal; and
(C) the resultant finely divided hydrogel has a weight-average particle diameter of 0.3 to 4 mm, and the ratio of coarse gel particles having particle diameters of not smaller than 10 mm is not more than 5 weight % of the finely divided hydrogel.

In the case where the polymerization is initiated at a temperature that is higher than an ordinary temperature and not lower than 30° C. and/or the polymerization initiator contains a transition metal in the prior polymerization, the stability of monomers is deteriorated before the polymerization. However, the above problem is also solved in the present invention in which the furfural is further used in an amount of 11 to 1,000 weight ppm. The water-soluble unsaturated monomer as used and the polymerization condition are in the above-mentioned range, and the static polymerization method such as belt polymerization (specifications of U.S. Pat. Nos. 6,241,928, 6,174,978, and 4,857, 610) can also be applied. However, the fine division is favorably carried out during the polymerization.

Furthermore, the present invention can also be favorably applied to the reversed-phase suspension polymerization.

That is to say, the present invention provides a production process for a water-absorbent resin, which comprises a polymerization step that includes the steps of: carrying out polymerization, involving crosslinking, of an aqueous solution of a water-soluble unsaturated monomer including acrylic acid (salt); and at the same time obtaining a finely divided hydrogel, with the production process being characterized in that the water-soluble unsaturated monomer contains furfural in an amount of 11 to 1,000 weight ppm (relative to the monomer). Then, as to the polymerization method, it is favorable that the polymerization, involving crosslinking, is reversed-phase suspension polymerization, and the present invention is a production process including the step of obtaining the resultant finely divided hydrogel at the same time as the suspension polymerization in an organic solvent The reversed-phase suspension polymerization is a polymerization method including the step of dispersing an aqueous monomer solution in a hydrophobic organic solvent in the form of particles having a weight-average particle diameter of about 1 to about 0.1 mm, and have the advantage of obtaining gel particles having particle diameters of products at the same time as the polymerization. Examples thereof are mentioned in US patents such as specifications of U.S. Pat. Nos. 4,093,776, 4,367,323, 4,446, 261, 4,683,274, and 5,244,735.

In the present invention, if necessary, dispersants selected from surfactants and protective colloids may be dissolved or dispersed in the aqueous solution of the water-soluble unsaturated monomer to contain them therein. In the case of particularly adopting the reversed-phase suspension polymerization in the present invention, containing this dispersant in the aqueous monomer solution causes the monomer or polymer to disperse in a particulate form in the hydrophobic organic solvent more uniformly, and then the particle diameter distribution of the water-absorbent resin as finally obtained becomes narrower.

As examples of these surfactants, one or at least two members as divisionally selected from nonionic surfactants (e.g. (polyoxyethylene)phosphates, such as polyoxyethylene octylphenyl ether phosphate and polyoxyethylene tridecyl ether phosphate (both produced by Dai-Ichi Industrial Pharmacy, trade name: PLYSURRF), polyoxyethylene alkyl ethers, polyoxyethylene alkyl phenyl ethers, polyoxyethylene alkyl esters, sorbitan fatty acid esters, polyoxyethylene sorbitan fatty acid esters, and sucrose fatty acid esters), and anionic surfactants (e.g. sulfate esters of higher alcohols, alkylnaphthalenesulfonic acid salts, alkyl polyoxyethylene sulfate salts, and dialkylsufosuccinic acid salts) can be used, and these can be added to the polymerization system in a lump or divisionally. Furthermore, examples of polymer protective colloids include ethyl cellulose, ethyl hydroxy-cellulose, maleic acid (maleic anhydride)-ethylene copolymers, and maleic acid (maleic anhydride)-butadiene copolymers. Of the above, fatty-acid-ester surfactants are favorable, and nonionic or anionic surfactants having a HLB value of not less than 8 are more favorable. The amount of the surfactant or dispersant as used is generally in the range of 0.05 to 10 weight %, favorably 0.5 to 5 weight %, relative to the water-soluble unsaturated monomer.

There is no especial limitation on the hydrophobic organic solvent as used in the present invention if it is not miscible with the aqueous monomer solution and forms two phases. Examples thereof include: aliphatic hydrocarbons, such as n-pentane, n-hexane, n-heptane, and n-octane; alicyclic hydrocarbons that may have a substituent group, such as cyclohexane, cyclooctane, methylcyclohexane, and decalin; and aromatic hydrocarbons that may have a substituent group, such as benzene, ethylbenzene, toluene, and xylene. These can be used either alone respectively or in combinations with each other. Particularly favorable is n-hexane, n-heptane, cyclohexane, methylcyclohexane, toluene, or xylene. The ratio of the hydrophobic organic solvent and the aqueous monomer solution is favorably 3:2 to 4:1 approximately. The dispersant or hydrophobic organic solvent may be added during or after the polymerization.

The monomer is dispersed in these solvents in a lump or divisionally, and then the solvent in which the monomer or its polymer is dispersed is heated favorably at 40 to 90° C., more favorably at 50 to 80° C., and thereby the polymerization may be favorably carried out for 0.5 to 10 hours, more favorably 1 to 5 hours. The weight-average particle diameter during the dispersing is usually in the range of 10 to 2,000 μm, favorably 100 to 1,000 μm in view of properties, more favorably 200 to 600 μm. Furthermore, the less the content of fine powders having particle diameters of not smaller than 850 μm and fine powders having particle diameters of not larger than 150 μm is (specifically, not more than 10 weight % each, and further not more than 5 weight %), the more favorable it is. These may be fitly adjusted by such as the kind or amount of the dispersant or solvent, stirring power, and further granulation.

The polymerization is also mildly controlled, and further white water-absorbent resin particles that are not substantially colored either are obtained as a surprising characteristic because the reversed-phase suspension polymerization is carried out in the present invention.

That is to say, it has been found that: in the polymerization method in the presence of the furfural in an amount of 11 to 1,000 weight ppm, the reversed-phase suspension polymerization is favorable for improving the coloring of the water-absorbent resin. When the concentration is raised (for example, the concentration of the aqueous monomer solution is not less than 40 weight %) in the reversed-phase suspension polymerization which is carried out by being dispersed in a large quantity of solvent, the scale-increased industrial production (for example, in a reaction vessel having not smaller than 1 m$^3$, particularly not smaller than 5 m$^3$) has hitherto been difficult because of danger of explosion of the polymerization, and the productivity has been low. However, the above problems are also solved by carrying out the polymerization in the presence of the furfural in an amount of 11 to 1,000 weight ppm, and the coexistence of the furfural further causes proper aggregation (granulation) of particles during the polymerization, thus obtaining a water-absorbent resin by the reversed-phase suspension polymerization, wherein the water-absorbent resin contains little fine particle and has a controlled particle diameter. In addition, as a great merit of the reversed-phase suspension polymerization, the water-absorbent resin is not colored even if the furfural is used, and obtained is a substantially white water-absorbent resin, namely having a Yellow-Index (YI) of favorably 0 to 10, more favorably 0 to 8, still more favorably 0 to 6. Incidentally, the measurement method of the color is mentioned in such as a gazette of JP-A-322846/1999 (a specification of EP 942014) and a gazette of JP-A-071529/1 999.

That is to say, the present invention also provides a water-absorbent resin having a YI of 0 to 10, which is obtained by a process including the step of carrying out polymerization, involving crosslinking, of an aqueous solution of a water-soluble unsaturated monomer including acrylic acid (salt) and furfural in an amount of 11 to 1,000 weight ppm (relative to the monomer). The above water-absorbent resin is obtained, for example, by the above reversed-phase suspension polymerization. However, in the case of using the aqueous solution polymerization, the water-absorbent resin can also be obtained by such as washing with water or a hydrophilic organic solvent after the polymerization, or by adding such as decoloring agents or bleaching agents on the market. In addition, the above water-absorbent resin more favorably displays the above-mentioned or below-mentioned various properties.

(6) Favorable Steps After Polymerization (Drying, Pulverization, and Surface-crosslinking After Polymerization):

The crosslinked gel polymer as obtained in the polymerization step is finely divided with such as a meat chopper or a gel pulverizer that is exemplified in Japanese Patent Application No. 232734/2001 if it is necessary. The polymer is more favorably dried, and pulverized and classified if necessary. The present invention water-absorbent resin has high properties, and therefore its properties are further improved after the above step.

In the present invention, the drying is a procedure of removing water content, and the resin solid content, which is determined from the amount as decreased by the drying (heating 1 g of powder at 180° C. for 3 hours), is adjusted to favorably not less than 80 weight %, more favorably the range of 85 to 99 weight %, still more favorably 90 to 98 weight %, particularly favorably 92 to 97 weight %. In addition, there is no especial limitation on the drying temperature, but it may be favorably adjusted to such as the range of 100 to 300° C., more favorably 150 to 250° C. As to the drying method, adoptable are various methods, such as heat drying, hot-wind drying, drying under reduced pressure, infrared drying, microwave drying, drum-dryer drying, azeotropic dehydration with hydrophobic organic solvents, and high-humidity drying with steam having high temperature, and there is no especial limitation on the drying method. However, favorable is the hot-wind drying with gas that contains steam having a dew point of 40 to 100° C., more favorably 50 to 90° C., when the aqueous solution polymerization is applied. In addition, the azeotropic dehydration is favorably applied to the reversed-phase suspension polymerization.

There is no especial limitation on the shape of the water-absorbent resin as obtained by the present invention process, and the shape may be in a shape of such as unshaped pulverized or spherical powder, or in a shape of gel, sheet, bar, fiber, or film. In addition, the water-absorbent resin may be combined with such as fibrous base materials or supported thereon.

When the water-absorbent resin is a powder, its weight-average particle diameter is usually in the range of 10 to 2,000 $\mu$m, favorably 100 to 1,000 $\mu$m in view of properties, more favorably 200 to 600 $\mu$m. Furthermore, the less the content of fine powders having particle diameters of not smaller than 850 $\mu$m and fine powders having particle diameters of not larger than 150 $\mu$m is (specifically, not more than 10 weight % each, and further not more than 5 weight %), the more favorable it is.

Subsequently, the surface-crosslinking in the present invention is further explained.

The surface-crosslinking of a water-absorbent resin is to make uniform crosslinked structure in a polymer, and to further make a portion having high crosslinking density on a surface layer of the water-absorbent resin.

The water-absorbent resin as obtained in the present invention has little water-extractable content and high absorption capacity, and therefore there are advantages in that: the excellent surface-crosslinking effect is obtained, and further the high properties or performance can be displayed.

Herein, the surface-crosslinking is to make uniform crosslinked structure in a resin, and besides, to make a portion having high crosslinking density on a surface layer, and it is carried out with the following surface-crosslinking agent. The surface-crosslinking agent may be permeated or coated onto the resin surface. The surface-crosslinking of the resin enhances absorption capacity and liquid permeability under a load.

The water-absorbent resin, according to the present invention, favorably displays an absorption capacity of not less than 20 g/g for a physiological saline under a load (4.9 kPa), more favorably not less than 23 g/g, still more favorably not less than 25 g/g. In addition, the present invention process can easily and stably produce a water-absorbent resin having high properties, which favorably displays an absorption capacity of not less than 20 g/g for a physiological saline under a load (1.9 kPa), more favorably not less than 25 g/g, still more favorably not less than 28 g/g, particularly favorably not less than 32 g/g, and which favorably displays an absorption capacity of not less than 25 g/g without load, more favorably not less than 28 g/g, particularly favorably not less than 32 g/g. In addition, the water-absorbent resin is thought to favorably display a liquid permeation amount (SFC) of not smaller than $10 \times 10^{-7}$, more favorably not smaller than $20 \times 10^{-7}$, still more favorably not smaller than $50 \times 10^{-7}$. Incidentally, these measurement methods are defined in the following examples.

As to the crosslinking agent for carrying out the above surface-crosslinking, there are used various agents, but generally used in view of properties are such as polyhydric alcohol compounds, epoxy compounds, polyamine compounds or their condensed products with haloepoxy compounds, oxazoline compounds, mono-, di-, or polyoxazolidinone compounds, multivalent metal salts, and alkylene carbonate compounds.

The surface-crosslinking agent as used in the present invention is specifically exemplified in such as specifications of U.S. Pat. Nos. 6,228,930, 6,071,976, and 6,254,990. Examples thereof include one or at least two of: polyhydric alcohol compounds, such as mono-, di-, tri-, tetra-, or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol; epoxy compounds, such as ethylene glycol diglycidyl ether and glycidol; polyamine compounds, such as ethylenediamine, diethylenetriamine, triethylenetetraamine, tetraethylenepentaamine, pentaethylenehexaamine, polyethylenimine, and polyamide polyamines; haloepoxy compounds, such as epichlorohydrin, epibromohydrin, and α-methylepichlorohydrin; condensed products of the above polyamine compounds and the above haloepoxy compounds; alkylene carbonate compounds such as ethylene carobnate; mono-, di-, or polyoxazolidione compounds such as 2-oxazolidione; oxazolidine compounds, such as 2-oxotetrahydro-1,3-oxdinene compounds and ethylenebisoxazoline; oxetane compounds such as 3-methyl-oxetane-3-methanol, but there is no especial limitation thereto. In addition, at least two of these agents may be used in combinations with each other. In order to display the effect of the present invention to the maximum, at least the polyhydric alcohol (a polyhydric alcohol favorably having 2 to 10 carbon atoms, more favorably 3 to 8 carbon atoms) is favorably used among these crosslinking agents.

The amount of the surface-crosslinking agent as used, depending upon such as the compounds as used and their combinations, is favorably in the range of 0.001 to 10 parts by weight, more favorably 0.01 to 5 parts by weight, relative to 100 parts by weight of the resin in terms of solid content.

In the present invention, water is favorably used when the surface-crosslinking is carried out. Then, the amount of the water as used, depending upon the water content of the water-absorbent resin as used, is usually in the range of favorably 0.5 to 20 parts by weight, more favorably 0.5 to 10 parts by weight, relative to 100 parts by weight of the water-absorbent resin. In addition, hydrophilic organic solvents may be used other than the water in the present invention. The amount of the hydrophilic organic solvent as used is favorably in the range of 0 to 10 parts by weight, more favorably 0 to 5 parts by weight, still more favorably 0 to 3 parts by weight, relative to 100 parts by weight of the water-absorbent resin. The temperature of a solution of the crosslinking agent is favorably adjusted to the range of 0° C. to a boiling point, more favorably 5 to 50° C., still more favorably 10 to 30° C., in view of blendability and stability. In addition, the temperature of the water-absorbent resin powder before blending is favorably in the range of 0 to 80° C., more favorably 40 to 70° C., in view of blendability.

Furthermore, among various blending methods in the present invention, favorable is a method which involves: blending with the water and/or hydrophilic organic solvent if necessary; and thereafter spraywise or dropwise blending (more favorably spraying) the resultant aqueous solution with the water-absorbent resin. The size of the liquid drop as sprayed is favorably not larger than 300 μm, more favorably not larger than 200 μm. In addition, water-insoluble fine particle powders or surfactants may coexist in such a range as not to hinder the effects of the present invention when the blending is carried out.

It is necessary that the favorable blending apparatus as used in the aforementioned blending can produce great blendability in order to ensure the uniform blending. As to the blending apparatus usable in the present invention, various blenders are used, but favorable is a high-speed stirring-type blender, particularly a high-speed stirring-type continuous blender. Specifically, Turbulizer (trade name) and (Lödige mixer) (trade name) are usable.

The water-absorbent resin is favorably heat-treated after the crosslinking agent is blended. As to the conditions for carrying out the above heat treatment, the heating temperature is favorably in the range of 100 to 250° C., more favorably 150 to 250° C., and the heating time is favorably in the range of 1 minute to 2 hours. The favorable examples of the combination of the temperature and the time are 180° C. and 0.1 to 1.5 hours, and 200° C. and 0.1 to 1 hour.

The heat treatment can be carried out with conventional dryers or heating furnaces. Examples of the dryers include groove-type blending dryers, rotary dryers, disc dryers, fluidized-bed dryers, air-stream-type dryers, and infrared dryers. In addition, if necessary, the water-absorbent resin may be cooled after the heating.

Incidentally, these surface-crosslinking methods are also mentioned in: various European patents, such as specifications of EP 0349240, EP 0605150, EP 0450923, EP 0812873, EP 0450924, and EP 0668080; various Japanese patents, such as gazettes of JP-A-242709/1995 and JP-A-224204/1995; various US patents, such as specifications of U.S. Pat. Nos. 5,409,771, 5,597,873, 5,385,983, 5,610,220, 5,633,316, 5,672,633, and 5,462,972; and various international published patents, such as pamphlets of WO 99/42494, WO 99/43720, and WO 99/42496, and these surface-crosslinking methods can also be applied to the present invention.

(7) Uses of Present Invention Water-absorbent Resin:

Various functions can also be given by adding, to the present invention water-absorbent resin, such as disinfectants, antimicrobial agents, perfumes, various inorganic powders, foaming agents, pigments, chelating agents, dyes, hydrophilic short fibers, manure, oxidants, reductants, water, and salts, in an amount of favorably not larger than 20 parts by weight, more favorably not larger than 10 parts by weight, in the production process or after the production. Favorable examples of the compounds as added include chelating agents, water-insoluble inorganic powders, and/or polyamines.

The present invention process enables easy production of the water-absorbent resin, which has good absorption properties that are excellent in balance of the absorption capacity without load, absorption capacity under a load, and extractable content. The water-absorbent resin is widely used for water-retaining agents in agricultural and horticultural fields, water-holding materials in engineering works fields, hygroscopic agents, moisture-removing agents, and building materials, but the water-absorbent resin is particularly favorably used for sanitary materials such as disposable diapers and sanitary napkins. Furthermore, the present invention water-absorbent resin is excellent in the above three properties, and therefore the sanitary materials can be used generally in a high concentration (e.g. 30 to 100 weight %, favorably 40 to 100 weight %, more favorably 50 to 95 weight %) as a concentration of the water-absorbent resin (weight ratio of the water-absorbent resin to the total of the water-absorbent resin and the fibrous base material).

DETAILED DESCRIPTION OF PREFERRED EMBODIMENTS

Hereinafter, the present invention is illustrated by the following examples. However, the present invention is not limited to the examples and not understood such. In addition, the various properties as mentioned in the claims and examples of the present invention were measured by the following methods.

(1) Absorption Capacity for Physiological Saline without Load:

The absorption capacity was determined according to the specification of U.S. Pat. No. 5,164,459. That is to say, to a nonwoven-fabric-made bag (60×60 mm), 200 mg of water-absorbent resin was uniformly added and sealed, and then immersed in 100 g of a 0.9 weight % physiological saline at 25 (±3) ° C. The bag was pulled up after 60 minutes, and the weight (W1(mg)) of the bag was measured after draining off at 250 G (250×9.81 m/sec$^2$) for 3 minutes with a centrifugal separator. The same procedure was carried out without using the water-absorbent resin, and then the weight (W2 (mg)) of the bag was measured. Then, the absorption capacity was calculated in accordance with the following equation:

absorption capacity (g/g) without load=($W1$–$W2$)/200

(2) Water-extractable Content:

Into 1,000 ml of deionized water at room temperature, 500 mg of water-absorbent resin was dispersed, and the resultant mixture was stirred with a magnetic stirrer having a size of 40 mm for 16 hours. Thereafter, the resultant swollen gel was separated and filtrated with filter paper (TOYO, No. 6). Subsequently, the colloidal titration of a water-soluble poly(acrylic acid salt) in the resultant filtrate as eluted from the water-absorbent resin was carried out with methyl glycol chitosan and potassium polyvinyl sulfate, and thereby the weight percentage of the water-extractable content in the water-absorbent resin (relative to the water-absorbent resin) was determined.

(3) Residual Monomer:

The separately prepared filtrate after being stirred for 2 hours in the above (2) was UV-analyzed with liquid chromatography, and thereby the amount of the residual monomer in the water-absorbent resin (weight ppm/relative to water-absorbent resin) was also analyzed.

(4) Absorption Capacity Under Load:

With referring to the specifications of U.S. Pat. Nos. 6,228,930, 6,071,976, and 6,254,990, the absorption capacity for a physiological saline under a load was determined.

According to the method as mentioned in the aforementioned US patents, a predetermined load (4.9 kPa) was applied to 0.900 g of water-absorbent resin, and the weight Wa (g) of the physiological saline as absorbed by the water-absorbent resin over a period of 60 minutes with the passage of time was determined from the measured value of a balance. Separately, the same procedure was carried out without using the water-absorbent resin, and the weight Wb (g) of the physiological saline as absorbed by such as a filter other than the water-absorbent resin was determined as a blank value from the measured value of the balance, and then the absorption capacity was calculated in accordance with the following equation:

absorption capacity (g/g) under a load of 4.9 kPa= ($Wa$–$Wb$)/0.900

(5) Liquid Permeability Under Load (Saline Flow Conductivity: SFC):

As to the measurement method for the liquid permeability under a load, according to the pamphlet of WO 95/22356, 0.9 g of water-absorbent resin was swollen for an hour under a load of 20 g/cm$^2$ (about 1.9 kPa), and thereafter the saline flow conductivity (abbreviated to SFC) of the resultant swollen gel for 0.0018M-NaCl solution (20 to 25° C.) under a load of 20 g/cm$^2$ (about 1.9 kPa) was determined. Incidentally, its unit is [cm$^3$·s·g$^{-1}$]. The larger the numeral value is, the larger the liquid permeability is.

(6) Peak Time and Induction Time:

The temperature of the monomer or polymerization gel during the polymerization was measured with a thermometer, and how long time passed since the addition of the initiator until the rise of temperature (minute) was defined as the induction time, and further how long time passed until the highest temperature of the polymerization system was defined as the peak time.

(7) Coarse Gel:

The finely divided crosslinked hydrogel polymer as obtained by the polymerization was maintained at 60 to 80° C., and the hydrogel was classified with a lattice that had an opening size of 10 mm and was coated with Teflon (registered trade mark), and then the weight percentage of the coarse gel as remained on the lattice (relative to the entire hydrogel) was determined.

(8) Weight-average Particle Diameter of Hydrogel:

The hydrogel was classified in a wet state to calculate its particle diameter distribution, and then the weight-average particle diameter (D50) was determined by plotting the particle diameter distribution on logarithmic probability paper.

(9) Color of Water-absorbent Resin Powder:

With referring to the gazettes of JP-A-322846/1999 (the specification of EP 942014) and JP-A-071529/1999, the color of the water-absorbent resin powder was measured as follows. That is to say, about 3 g of water-absorbent resin powder as obtained were all filled into a paste sample stand (30 mm Φ), and then the surface color of the water-absorbent resin was measured in terms of the coloring degree (YI) with a spectral color difference meter, SZ-Σ80 COLOR MEASURING SYSTEM (produced by Nippon Denshoki Kogyo Co., Ltd.), under the setting conditions (reflection measurement/attached powder-paste sample stand (30 mm Φ)/standard circular white plate NO2 for powder-paste as the standard/30 Φ floodlight pipe).

EXAMPLE 1

Prepared was an aqueous solution (1) of a water-soluble unsaturated monomer with a concentration of 40 weight %, including 451.7 g of acrylic acid, 4,780.3 g of 37 weight % aqueous sodium acrylate solution, 8.5481 g of polyethylene glycol diacrylate (average polyethylene glycol unit number: 8) as an internal-crosslinking agent, furfural in an amount of 201.6 weight ppm (relative to the monomer in terms of solid content), and 275.4 g of water.

The above aqueous solution (1) of the water-soluble unsaturated monomer containing the furfural in an amount of 201.6 weight ppm was supplied to a reactor as prepared by lidding a jacketed stainless twin-arm kneader of 10 liters in capacity with two sigma-type blades as a polymerization vessel having shear force, and the atmosphere in the reactor was replaced with nitrogen for 20 minutes while the above aqueous solution was maintained at 25° C. Subsequently, while warm water of 25° C. was passed under a stream of nitrogen and the blades were rotated, 22.6 g of 20 weight % aqueous sodium persulfate solution and 12.5 g of 1.0 weight % aqueous L-ascorbic acid solution were added to the reactor. As a result, the polymerization was initiated after 20 seconds. The warm water of the jacket was heated to 70° C. at the same time as the initiation of the polymerization, and the resultant crosslinked hydrogel polymer was sheared while the polymerization was carried out. After 10.5 minutes, the reaction system reached its peak temperature, and then the polymerization was completed after 20 minutes since the peak temperature was shown.

A crosslinked hydrogel polymer (1) as obtained in this way was finely divided in a particulate form, and the ratio of coarse gel particles having particle diameters of not smaller than 10 mm was 0 weight % of the entirety.

Next, the above particulate crosslinked hydrogel polymer (1) was spread on a wire gauze with a mesh opening size of 300 μm to form a layer of about 50 mm in thickness. Subsequently, the hydrogel was hot-wind-dried by passing a hot wind having a temperature of 170° C. (dew point: 50° C.) at a speed of 1 m/sec through the hydrogel in its vertical direction for 1 hour. Pulverized was a block-shaped dried material which was obtained in this way and comprised of a particulate dry polymer, and further the resultant pulverized product was classified with a JIS standard sieve having a mesh opening size of 850 μm, thus obtaining a water-absorbent resin powder (1). The results are listed in Table 1.

EXAMPLE 2

Prepared was an aqueous solution (2) of a water-soluble unsaturated monomer with a concentration of 40 weight %, including 513.6 g of acrylic acid, 4,544.5 g of 37 weight % aqueous sodium acrylate solution, 8.5481 g of polyethylene glycol diacrylate (average polyethylene glycol unit number: 8) as an internal-crosslinking agent, furfural in an amount of 205.3 weight ppm (relative to the monomer in terms of solid content), and 393.4 g of water.

The above aqueous monomer solution (2) containing the furfural in an amount of 205.3 weight ppm was supplied to the same polymerization vessel as of Example 1, and the atmosphere in the reactor was replaced with nitrogen for 20 minutes while the above aqueous solution was maintained at 40° C. Subsequently, while warm water of 40° C. was passed and the blades were rotated, 22.6 g of 20 weight % aqueous sodium persulfate solution and 12.5 g of 1.0 weight % aqueous L-ascorbic acid solution were added to the reactor. As a result, the polymerization was initiated after 10 seconds. The warm water was heated to 60° C. at the same time as the initiation of the polymerization, and the resultant crosslinked hydrogel polymer was sheared while the polymerization was carried out. After 9.0 minutes, the reaction system reached its peak temperature, and thereafter the polymerization was completed after 20 minutes since the peak was reached.

A crosslinked hydrogel polymer (2) as obtained was finely divided in a particulate form, and the ratio of coarse gel particles having particle diameters of not smaller than 10 mm was 0 weight % of the entirety. Since then, the drying, pulverization, and classification were carried out in the same way as of Example 1, thus obtaining a water-absorbent resin powder (2). The results are listed in Table 1.

Comparative Example 1

The aqueous solution of the water-soluble unsaturated monomer as prepared in Example 1 was changed, and thereby prepared was a comparative aqueous water-soluble monomer solution (1) with a concentration of 40 weight %, in which the furfural amount was adjusted to 0.3 weight ppm (relative to the monomer in terms of solid content).

The above comparative aqueous water-soluble monomer solution (1) containing the furfural in an amount of 0.3 weight ppm was supplied to the reactor as mentioned in Example 1. Since then, the atmosphere in the reactor was replaced with nitrogen in the same way as of Example 1, and the sodium persulfate and L-ascorbic acid were similarly added thereto. As a result, the polymerization was initiated after 10 seconds. The warm water was heated to 60° C. at the same time as the initiation of the polymerization. After 8.5 minutes, the reaction system reached its peak temperature, and thereafter the resultant crosslinked hydrogel polymer was sheared while the polymerization was carried out. The polymerization was completed after 20 minutes since the peak temperature was shown.

The major proportion of the resultant comparative hydrogel polymer (1) was in the form of particles having particle diameters of about 1 mm in the same way as of Example 1, but the polymer was not finely divided sufficiently, and a coarse gel was partially observed therein. The hydrogel (coarse gel) particles having particle diameters of not smaller than 10 mm existed in an amount of 8.0 weight % of the entirety.

Subsequently, the comparative particulate crosslinked hydrogel polymer (1) was dried for 1 hour in the same way as of Example 1, but the contaminated coarse gel could not be dried sufficiently. In the case of the drying time of 1 hour, the dried polymer was contaminated with a few percents of an undried product, and therefore the drying was imperfect. In addition, the subsequent pulverization and classification procedures were impossible because of the adhesion of the undried product. The results are listed in Table 1.

Comparative Example 2

In Comparative Example 1, the dried polymer contaminated with a few percents of the undried product was further dried for an hour. Specifically, the comparative particulate crosslinked hydrogel polymer (1) was dried for 2 hours and thereafter pulverized in the same way as of Example 1, thus obtaining a comparative water-absorbent resin powder (2). The results are listed in Table 1.

EXAMPLE 3

Prepared was an aqueous solution (3) of a water-soluble unsaturated monomer with a concentration of 40 weight %, including 447.6 g of acrylic acid, 4,736.5 g of 37 weight % aqueous sodium acrylate solution, 8.4657 g of polyethylene glycol diacrylate (average polyethylene glycol unit number: 8) as an internal-crosslinking agent, furfural in an amount of 205.3 weight ppm (relative to the monomer in terms of solid content), and 270.5 g of water. The above aqueous monomer solution (3) containing the furfural in an amount of 205.3 weight ppm was supplied to the same reactor as of Example 1, and the atmosphere in the reactor was replaced with nitrogen for 20 minutes while the above aqueous solution was maintained at 25° C.

Subsequently, while warm water of 25° C. was passed and the blades were rotated, 2.2 g of 0.1 weight % aqueous solution of $Fe^{+3}$ standard solution was added thereto first so that the concentration would be 1 weight ppm (in terms of Fe) relative to the monomer in terms of solid content, and 22.4 g of 20 weight % aqueous sodium persulfate solution and 12.4 g of 1.0 weight % aqueous L-ascorbic acid solution as initiators were further added thereto. As a result, the polymerization was initiated after 20 seconds. The warm water was heated to 60° C. at the same time as the initiation of the polymerization, and the resultant crosslinked hydrogel polymer was sheared while the polymerization was carried out. After 11.5 minutes, the reaction system reached its peak temperature, and thereafter the polymerization was completed after 20 minutes since the peak was reached.

A crosslinked hydrogel polymer (3) as obtained was finely divided in a particulate form, and the ratio of coarse gel particles having particle diameters of not smaller than 10 mm was 0. weight % of the entirety. Since then, the drying, pulverization, and classification were carried out in the same way as of Example 1, thus obtaining a water-absorbent resin powder (3). The results are listed in Table 1.

TABLE 1

| | Furfural (weight ppm) | Temperature (° C.) | Coarse gel (weight %) | Absorption capacity (g/g) | Water-extractable content (weight %) |
|---|---|---|---|---|---|
| Example 1 | 203.4 | 25 | 0 | 39.7 | 11.6 |
| Example 2 | 205.3 | 40 | 0 | 40.2 | 12.2 |
| Example 3 | 205.3 | 25 | 0 | 39.4 | 14.3 |
| Comparative Example 1 | 0.3 | 25 | 8.0 | (Not sufficiently dried or could not be pulverized) | |
| Comparative Example 2 | 0.3 | 25 | 8.0 | 41.0 | 12.0 |

As is shown in Table 1, in the production process for a water-absorbent resin, which comprises a polymerization step that includes the steps of: carrying out polymerization, involving crosslinking, of an aqueous solution of a water-soluble unsaturated monomer including acrylic acid (salt); and at the same time carrying out fine division of the resultant hydrogel, the water-soluble unsaturated monomer contains furfural in an amount of 11 to 1,000 weight ppm (relative to the monomer in terms of solid content), and thereby a coarse gel is not formed at all or hardly formed during the polymerization. As a result, the polymerization time and drying time are shortened, and further the properties are also enhanced, and the stop of the pulverization step and classification step after the drying caused by an undried product can also be prevented.

EXAMPLE 4

To 500 g of the water-absorbent resin powder (1) as obtained in Example 1, an aqueous surface-crosslinking agent solution including 1,4-butanediol, propylene glycol, and water in amounts of 0.32 weight %, 0.5 weight %, and 2.73 weight % (relative to the powder) respectively was added, and the resultant mixture was heat-stirred for 35 minutes in a mixer as heated in an oil bath at 212° C., thus obtaining a surface-crosslinked water-absorbent resin powder (4). The results are listed in Table 2.

TABLE 2

| | Absorption capacity (g/g) | Absorption capacity under load (g/g) |
|---|---|---|
| Example 4 | 33.2 | 26.6 |

As is shown in Table 2, the excellent surface-crosslinking effect is displayed.

EXAMPLE 5

Prepared was an aqueous solution (5) of a water-soluble unsaturated monomer with a concentration of 40 weight %, including 21.62 g of acrylic acid, 228.77 g of 37 weight % aqueous sodium acrylate solution, 0.292 g of polyethylene glycol diacrylate (average polyethylene glycol unit number: 8) as an internal-crosslinking agent, furfural in an amount of 203.5 weight ppm (relative to the monomer in terms of solid content), and 13.11 g of water.

Subsequently, the above aqueous solution was added to a cylindrical polypropylene vessel of about 500 ml in capacity after the atmosphere in the vessel was replaced with nitrogen for 30 minutes while the above aqueous solution was maintained at 40° C. The above polymerization vessel was lidded and heat-retained at 40° C. in an atmosphere of nitrogen, and then 1.44 g of 10 weight % aqueous sodium persulfate solution and 0.43 g of 0.5 weight % aqueous L-ascorbic acid solution as polymerization initiators were added thereto. As a result, the polymerization was initiated after 10 seconds. After 11 minutes, the peak temperature was shown, and thereafter the polymerization was completed after 10 minutes since the peak temperature was shown.

The resultant crosslinked hydrogel polymer (5) was cut into small pieces having sizes of a few millimeters, and hot-wind-dried at 170° C. for 30 minutes, and thereafter the resultant dried product was pulverized with a vibration mill, and further the resultant pulverized product was classified with a JIS standard sieve having a mesh opening size of 850 μm, thus obtaining a water-absorbent resin powder (5). The results are listed in Table 3.

Comparative Example 3

The replacement with nitrogen was carried out in the same way as of Example 5 except that the temperature of the water-soluble unsaturated monomer (5) was changed from 40° C. to 20° C. Since then, the polymerization initiators were added to the water-soluble unsaturated monomer (5) of 20° C. in the same way as of Example 3. As a result, the polymerization was initiated after 30 seconds, and the temperature was raised by the polymerization heat. However, it took 84 minutes to reach the peak temperature, and the polymerization was completed after 10 minutes since the peak temperature was shown. The resultant comparative crosslinked hydrogel polymer (3) was cut and dried in the same way as of Example 5, and thereafter they were pulverized and classified similarly, thus obtaining a comparative water-absorbent resin powder (3). The results are listed in Table 3.

EXAMPLE 6

The replacement with nitrogen was carried out in the same way as of Example 5 except that the temperature of the water-soluble unsaturated monomer (5) was changed from 40° C. to 20° C. Since then, 1.063 g of $Fe^{+3}$ standard solution (Fe ion concentration: 100 weight ppm) on the market was added to the water-soluble unsaturated monomer (6) of 20° C. so that the concentration would be 1 weight ppm of $Fe^{+3}$ relative to the monomer in terms of solid content, and thereafter 1.44 g of 10 weight % aqueous sodium persulfate solution and 0.43 g of 0.5 weight % aqueous L-ascorbic acid solution as polymerization initiators were added thereto. As a result, the polymerization was initiated after 10 seconds, and the peak temperature was shown after 34 minutes. The polymerization was completed after 10 minutes since the peak temperature was shown.

The resultant crosslinked hydrogel polymer (6) was cut and dried in the same way as of Example 5, and thereafter they were pulverized and classified similarly, thus obtaining a water-absorbent resin powder (6). The results are listed in Table 3.

TABLE 3

| | Temperature (° C.) | Transition metal (weight ppm) | Induction time (sec) | Peak time (min) | Absorption capacity (g/g) | Water-extractable content (weight %) |
|---|---|---|---|---|---|---|
| Example 5 | 40 | None | 10 | 11 | 47.2 | 15.7 |
| Comparative Example 3 | 20 | None | 30 | 84 | 45.3 | 15.9 |
| Example 6 | 20 | 1 | 10 | 34 | 50.0 | 21.4 |

As is shown in Table 3, the use of the furfural also enables the polymerization such as the high-temperature polymerization or polymerization in the presence of a transition metal stably.

EXAMPLE 7

An aqueous solution (7) of a water-soluble unsaturated monomer with a monomer concentration of 35 weight % and a neutralization ratio of 75% was obtained by using 18.0 g of acrylic acid, 190.6 g of 37 weight % aqueous sodium acrylate solution having a furfural content of 70 weight ppm (in terms of solid content), 0.2435 g of polyethylene glycol diacrylate (average polyethylene glycol unit number: 8) as an internal-crosslinking agent, and 43.1 g of deionized water. Into this aqueous monomer solution (7), 0.048 g of sodium persulfate was dissolved, and the dissolved oxygen was removed by blowing nitrogen gas.

A four-necked separable flask equipped with a stirrer, a reflux condenser, a thermometer, a nitrogen-introducing tube, and a dropping funnel was charged with 389.5 g of cyclohexane, and 1.77 g of ethyl cellulose (produced by HERCULES IC., N-200) as a dispersant was added thereto and dissolved, and then the dissolved oxygen was removed by blowing nitrogen gas. Subsequently, the aqueous monomer solution (7) was added to the above separable flask, and the resultant mixture was dispersed with stirring at 225 rpm. Thereafter, the bath temperature was raised to 65° C. in order to initiate polymerization, and thereafter the polymerization was completed after this temperature was retained for 2 hours. After the end of the polymerization, the major proportion of water in the resultant hydrogel was distilled out by the azeotropic dehydration with the cyclohexane. Thereafter, the resultant residue was filtrated and further dried under reduced pressure at 80° C., thus obtaining a spherical water-absorbent resin powder (7). The results are listed in Table 4.

EXAMPLE 8

An aqueous solution (8) of a water-soluble unsaturated monomer with a monomer concentration of 40 weight % and a neutralization ratio of 75% was obtained by using 18.0 g of acrylic acid having a furfural content of 250 ppm, 190.6 g of 37 weight % aqueous sodium acrylate solution having a furfural content of 190 weight ppm (in terms of solid content), 0.2435 g of polyethylene glycol diacrylate (average polyethylene glycol unit number: 8) as an internal-crosslinking agent, and 11.0 g of deionized water. Into this aqueous monomer solution (8), 0.072 g of sodium persulfate was dissolved, and the dissolved oxygen was removed by blowing nitrogen gas.

A four-necked separable flask equipped with a stirrer, a reflux condenser, a thermometer, a nitrogen-introducing tube, and a dropping funnel was charged with 389.5 g of cyclohexane, and 1.77 g of ethyl cellulose (produced by HERCULES INC., N-200) as a dispersant was added thereto and dissolved, and the dissolved oxygen was removed by blowing nitrogen gas. Subsequently, the aqueous monomer solution (8) was added to the above separable flask, and the resultant mixture was dispersed with stirring at 225 rpm. Thereafter, the bath temperature was raised to 65° C. in order to initiate polymerization, and thereafter the polymerization was completed after this temperature was retained for 2 hours. After the end of the polymerization, the major proportion of water in the resultant hydrogel was distilled out by the azeotropic dehydration with the cyclohexane. Thereafter, the resultant residue was filtrated and further dried under reduced pressure at 80° C., thus obtaining a spherical water-absorbent resin powder (8). The results are listed in Table 4.

TABLE 4

| | Temperature (° C.) | Absorption capacity (g/g) | Water-extractable content (weight %) | YI |
|---|---|---|---|---|
| Example 7 | 65 | 40.9 | 11.2 | 4.39 |
| Example 8 | 65 | 41.6 | 17.1 | 5.21 |

As is shown in Table 4, the use of the furfural also enables the polymerization such as the high-temperature polymerization or high-concentration polymerization mildly, and further a water-absorbent resin, which is not substantially colored and has a YI value of not more than 10, is obtained in the reversed-phase suspension polymerization.

INDUSTRIAL APPLICATION

The present invention can provide a production process in which a coarse gel itself is made not to form, in a production process for a water-absorbent resin, which comprises a polymerization step that includes the steps of: carrying out polymerization, involving crosslinking, of an aqueous solution of a water-soluble unsaturated monomer including acrylic acid (salt); and at the same time carrying out fine division of the resultant hydrogel, or in a production process for a water-absorbent resin, which comprises the steps of: carrying out polymerization, involving crosslinking, of an aqueous solution of a water-soluble unsaturated monomer including acrylic acid (salt); and carrying out fine division of the resultant hydrogel. In addition, when the reversed-phase suspension polymerization is applied, the polymerization of the water-absorbent resin is also controlled mildly, and further the coloring is not substantially caused. Furthermore, the present invention can provide a production process which can solve the problems such that the stability of the monomer is deteriorated when the high-temperature polymerization or polymerization in the presence of a transition metal is carried out, in a production process for a water-absorbent resin, comprising the steps of: carrying out polymerization, involving crosslinking, of an aqueous solution of a water-soluble unsaturated monomer including acrylic acid (salt); and carrying out fine division of the resultant hydrogel.

The invention claimed is:

1. A production process for a water-absorbent resin, which comprises a polymerization step that includes the steps of: carrying out polymerization, involving crosslinking, of an aqueous solution of a water-soluble unsaturated monomer including acrylic acid (salt); and at the same time carrying out fine division to obtain a resultant hydrogel,
with the production process being characterized in that the water-soluble unsaturated monomer contains furfural in an amount of 11 to 1,000 weight ppm (relative to the monomer).

2. A production process for a water-absorbent resin, which comprises the steps of: carrying out polymerization, involving crosslinking, of an aqueous solution of a water-soluble unsaturated monomer including acrylic acid (salt); and carrying out fine division to obtain a resultant hydrogel,
wherein the polymerization, involving crosslinking, is aqueous solution polymerization, and the resultant finely divided hydrogel is obtained by the fine division after static polymerization on a moving belt,
with the production process being characterized in that:
(A) the water-soluble unsaturated monomer contains furfural in an amount of 11 to 1,000 weight ppm (relative to the monomer);
(B 1) the polymerization is initiated at a temperature of the aqueous solution of a water-soluble unsaturated monomer before a polymerization initiator is added of not lower than 30° C. and/or (B2) the water-soluble unsaturated monomer before a polymerization initiator is added further contains a transition metal in the range of not more than 5 ppm relative to the monomer in terms of its cation; and
(C) the resultant finely divided hydrogel has a weight-average particle diameter of 0.3 to 4 mm, and the ratio of coarse gel particles having particle diameters of not smaller than 10 mm is not more than 5 weight % of the finely divided hydrogel.

3. A production process for a water-absorbent resin, which comprises a polymerization step that includes the steps of: carrying out polymerization, involving crosslinking, of an aqueous solution of a water-soluble unsaturated monomer including acrylic acid (salt); and at the same time obtaining a finely divided hydrogel,
wherein the polymerization, involving crosslinking, is reversed-phase suspension polymerization, and the resultant finely divided hydrogel is obtained at the same time as the suspension polymerization in a hydrophobic organic solvent,
with the production process being characterized in that the water-soluble unsaturated monomer contains furfural in an amount of 11 to 1,000 weight ppm (relative to the monomer).

4. A production process according to claim 1, wherein the polymerization, involving crosslinking, is aqueous solution polymerization, and wherein the resultant finely divided hydrogel is obtained at the same time as the polymerization in a polymerization vessel having shear force.

5. A production process according to claim 1, wherein the polymerization step is continuous polymerization that involves continuously supplying the aqueous solution of the water-soluble unsaturated monomer and continuously discharging the resultant hydrogel.

6. A production process according to claim 2, wherein the polymerization step is continuous polymerization that involves continuously supplying the aqueous solution of the water-soluble unsaturated monomer and continuously discharging the resultant hydrogel.

7. A production process according to claim 3, wherein the polymerization step is continuous polymerization that involves continuously supplying the aqueous solution of the water-soluble unsaturated monomer and continuously discharging the resultant hydrogel.

8. A production process according to claim 1, wherein the aqueous solution of the water-soluble unsaturated monomer has a concentration of not less than 40 weight %.

9. A production process according to claim 2, wherein the aqueous solution of the water-soluble unsaturated monomer has a concentration of not less than 40 weight %.

10. A production process according to claim 3, wherein the aqueous solution of the water-soluble unsaturated monomer has a concentration of not less than 40 weight %.

11. A production process according to claim 1, wherein the polymerization of the aqueous solution of the water-soluble unsaturated monomer is initiated at a temperature of not lower than 40° C.

12. A production process according to claim 2, wherein the polymerization of the aqueous solution of the water-soluble unsaturated monomer is initiated at a temperature of not lower than 40° C.

13. A production process according to claim 3, wherein the polymerization of the aqueous solution of the water-soluble unsaturated monomer is initiated at a temperature of not lower than 40° C.

14. A production process according to claim 1, wherein the finely divided hydrogel resultant from the polymerization step has a weight-average particle diameter of 0.3 to 4 mm, and wherein the ratio of coarse gel particles having particle diameters of not smaller than 10 mm is not more than 5 weight % of the finely divided hydrogel.

15. A production process according to claim 3, wherein the finely divided hydrogel resultant from the polymerization step has a weight-average particle diameter of 0.3 to 4 mm, and wherein the ratio of coarse gel particles having particle diameters of not smaller than 10 mm is not more than 5 weight % of the finely divided hydrogel.

16. A production process according to claim 1, wherein the aqueous solution of the water-soluble unsaturated monomer further contains an aldehyde compound other than the furfural.

17. A production process according to claim 2, wherein the aqueous solution of the water-soluble unsaturated monomer further contains an aldehyde compound other than the furfural.

18. A production process according to claim 3, wherein the aqueous solution of the water-soluble unsaturated monomer further contains an aldehyde compound other than the furfural.

19. A production process according to claim 1, wherein the aqueous solution of the water-soluble unsaturated monomer further contains a methoxyphenol.

20. A production process according to claim 2, wherein the aqueous solution of the water-soluble unsaturated monomer further contains a methoxyphenol.

21. A production process according to claim 3, wherein the aqueous solution of the water-soluble unsaturated monomer further contains a methoxyphenol.

22. A production process according to claim 1, wherein the polymerization is carried out in the presence of a transition metal.

23. A production process according to claim 2, wherein the polymerization is carried out in the presence of a transition metal.

24. A production process according to claim 3, wherein the polymerization is carried out in the presence of a transition metal.

25. A water-absorbent resin as obtained by the production process as recited in claim 1, which displays an absorption capacity of not less than 20 g/g for a physiological saline under a load of 4.9 kPa.

26. A water-absorbent resin as obtained by the production process as recited in claim 2, which displays an absorption capacity of not less than 20 g/g for a physiological saline under a load of 4.9 kPa.

27. A water-absorbent resin as obtained by the production process as recited in claim 3, which displays an absorption capacity of not less than 20 g/g for a physiological saline under a load of 4.9 kPa.

28. A sanitary article, which comprises the water-absorbent resin as recited in claim 25.

29. A sanitary article, which comprises the water-absorbent resin as recited in claim 26.

30. A sanitary article, which comprises the water-absorbent resin as recited in claim 27.

31. A production process according to claim 3, wherein the aqueous solution of the water-soluble unsaturated monomer contains a dispersant selected from surfactants and protective colloids in the range of 0.05 to 10 weight % relative to the water-soluble unsaturated monomer.

32. A production process according to claim 3, wherein the hydrophobic organic solvent is selected from the group consisting of n-hexane, n-heptane, cyclohexane, methylcyclohexane, toluene and xylene.

33. A production process according to claim 3, wherein the reversed-phase suspension polymerization is carried out in the state that the hydrophobic organic solvent is heated at 40 to 900° C.

34. A production process according to claim 3, wherein a predetermined aggregation or granulation of particles occurs during the reversed-phase suspension polymerization.

35. A production process according to claim 3, wherein the water-absorbent resin has a Yellow-Index of 0 to 10.

36. A production process according to claim 1, wherein the water-extractable content in the water-absorbent resin is not more than 15 weight %.

37. A production process according to claim 2, wherein the transition metal is trivalent iron ion ($Fe^{3+}$).

38. A production process according to claim 1, further comprising the step of adding furfural to said monomer to obtain said monomer containing furfural in said amount of 11 to 1,000 weight ppm.

* * * * *